(12) United States Patent
Missotten

(10) Patent No.: US 7,771,262 B2
(45) Date of Patent: Aug. 10, 2010

(54) APPARATUS FOR ANALYSING COMPOSITION OF CROPS IN A CROP ELEVATOR

(75) Inventor: Bart M. A. Missotten, Winksele (BE)

(73) Assignee: CNH America LLC, New Holland, PA (US)

( * ) Notice: Subject to any disclaimer, the term of this patent is extended or adjusted under 35 U.S.C. 154(b) by 0 days.

(21) Appl. No.: 12/454,594

(22) Filed: May 20, 2009

(65) Prior Publication Data

US 2009/0291723 A1 Nov. 26, 2009

(30) Foreign Application Priority Data

May 22, 2008 (EP) .................................. 08156711

(51) Int. Cl.
*A01F 12/46* (2006.01)
(52) U.S. Cl. ....................................................... 460/114
(58) Field of Classification Search ................. 193/2 R, 193/23; 198/307.1, 311, 550.11; 460/114; 73/73, 861.73
See application file for complete search history.

(56) References Cited

U.S. PATENT DOCUMENTS

| | | | |
|---|---|---|---|
| 1,947,011 A | * | 2/1934 | Karthauser .................. 193/2 R |
| 3,182,903 A | * | 5/1965 | Marton ...................... 232/43.1 |
| 4,185,644 A | * | 1/1980 | Heitmann et al. ......... 131/109.3 |

FOREIGN PATENT DOCUMENTS

| | | |
|---|---|---|
| EP | 0908086 | 4/1999 |
| EP | 1053671 | 11/2000 |
| EP | 1892520 | 2/2008 |
| WO | WO 2006010761 | 2/2006 |
| WO | WO 2006010761 A1 * | 2/2006 |

* cited by examiner

*Primary Examiner*—Alicia M Torres
(74) *Attorney, Agent, or Firm*—Michael G. Harms; John William Stader; Patrick M. Sheldrake

(57) ABSTRACT

An apparatus for analyzing crop composition of crops moving in a grain elevator, the elevator including paddles moving up on an up-going side of the elevator and down on a down-going side of the elevator, the apparatus including a crop entrance for entry of crops from the up-going paddles to the analyzing apparatus and a housing for containing a portion of crops to be analyzed. The crop entrance is located in a plane parallel to the elevator's outer wall at the up-going side of the elevator. The apparatus further includes a sloped gutter portion for bringing crops from the crop entrance towards the housing.

8 Claims, 7 Drawing Sheets

APPARATUS FOR ANALYSING COMPOSITION OF CROPS IN A CROP ELEVATOR

CROSS REFERENCE TO RELATED APPLICATIONS

This Patent Application claims priority under 35 U.S.C. §119 to EP 08.156.711.7, filed on May 22, 2008 titled, "APPARATUS FOR ANALYSING COMPOSITION OF CROPS IN A CROP ELEVATOR" and having Bart M. A. Missotten as inventor. The full disclosure of EP 08.156.711.7 is hereby fully incorporated herein by reference.

FIELD OF THE INVENTION

The present invention is related to an apparatus for analysing crop composition, installed in conjunction with a crop elevator of a combine harvester.

STATE OF THE ART

Document WO2006/010761 is related to a crop analyser, comprising a light source and a camera for capturing sequential images of crops, which move along a path. The path is defined by the paddles of a clean grain elevator as is typically known in a combine harvester, the paddles moving up and down on a flexible drive chain to bring the crops (typically grain) from a lowermost point in the harvester to an uppermost point. The analysis apparatus comprises a housing attached to the side of the elevator, and comprises a grain entrance, a grain level sensor, a camera attached to a side window of the housing, and an auger defining a grain return path. Grain moving upward in the elevator and carried by the up-going paddles, falls through the grain entrance into the analyser housing, fills up the space of the housing up to the level sensor, at which point an image is taken by the camera. After that, the housing is emptied by actuating the auger, whereby the grain is moved towards the down-going paddles and taken back down the elevator. A next batch of grain then enters the housing for subsequent image-taking.

The location of the grain entrance into the analyser housing is such that a constant grain supply into the analyser is not ensured, e.g. when the harvester is on a sloped surface. This leads to difficulties in terms of reliability and frequency of the image-taking.

AIMS OF THE INVENTION

The present invention aims to provide a crop analysing apparatus attached to a crop elevator, that ensures a constant and reliable supply of crops into the apparatus.

SUMMARY OF THE INVENTION

The invention is related to an apparatus as disclosed in claim 1. Preferred embodiments are disclosed in combinations of claim 1 with one or more dependent claims. When the entrance into the analysing apparatus is located in a plane parallel to the elevator's outer plane at the up-going side of the elevator, the crops fall more easily into this entrance, and subsequently slide down the sloped gutter portion, so that a constant supply of crops is ensured. It is advantageous to place the grain entrance and gutter portion well above the housing, and to provide the housing with a sufficient height above the area where the crops are analysed (usually this is the area where a window and camera are present). In this way, there is always at least one full fresh batch of crop available for analysis after each preceding analysis step.

DETAILED DESCRIPTION OF PREFERRED EMBODIMENTS THE INVENTION

Figure 1:
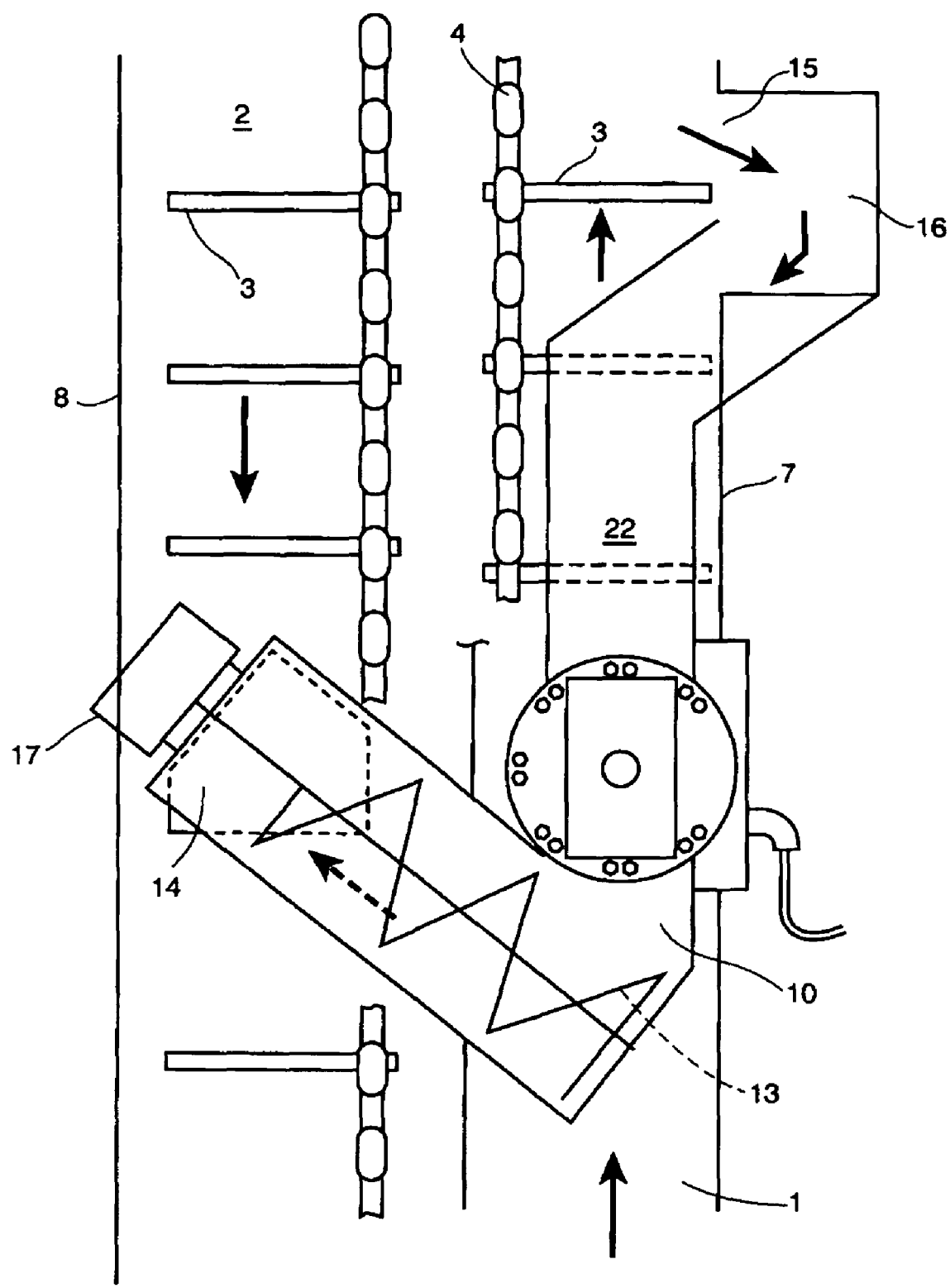
FIG. 1 is a schematic elevational view from one direction of a clean grain elevator and return auger of a combine harvester and showing the location of the apparatus according to the invention.

As seen in FIG. 1, the apparatus of the invention may be mounted on the side of a grain elevator, the elevator comprising an up-going path 1 and a down-going path 2. The grain elevator typically is installed on a side surface of a combine harvester to transport grain from a grain cleaning arrangement located in a lower part of the combine to a grain storage tank on top of the combine. In the grain elevator, paddles 3 are attached to an endless chain 4 for moving the paddles in the opposite directions as shown.

Figure 2:
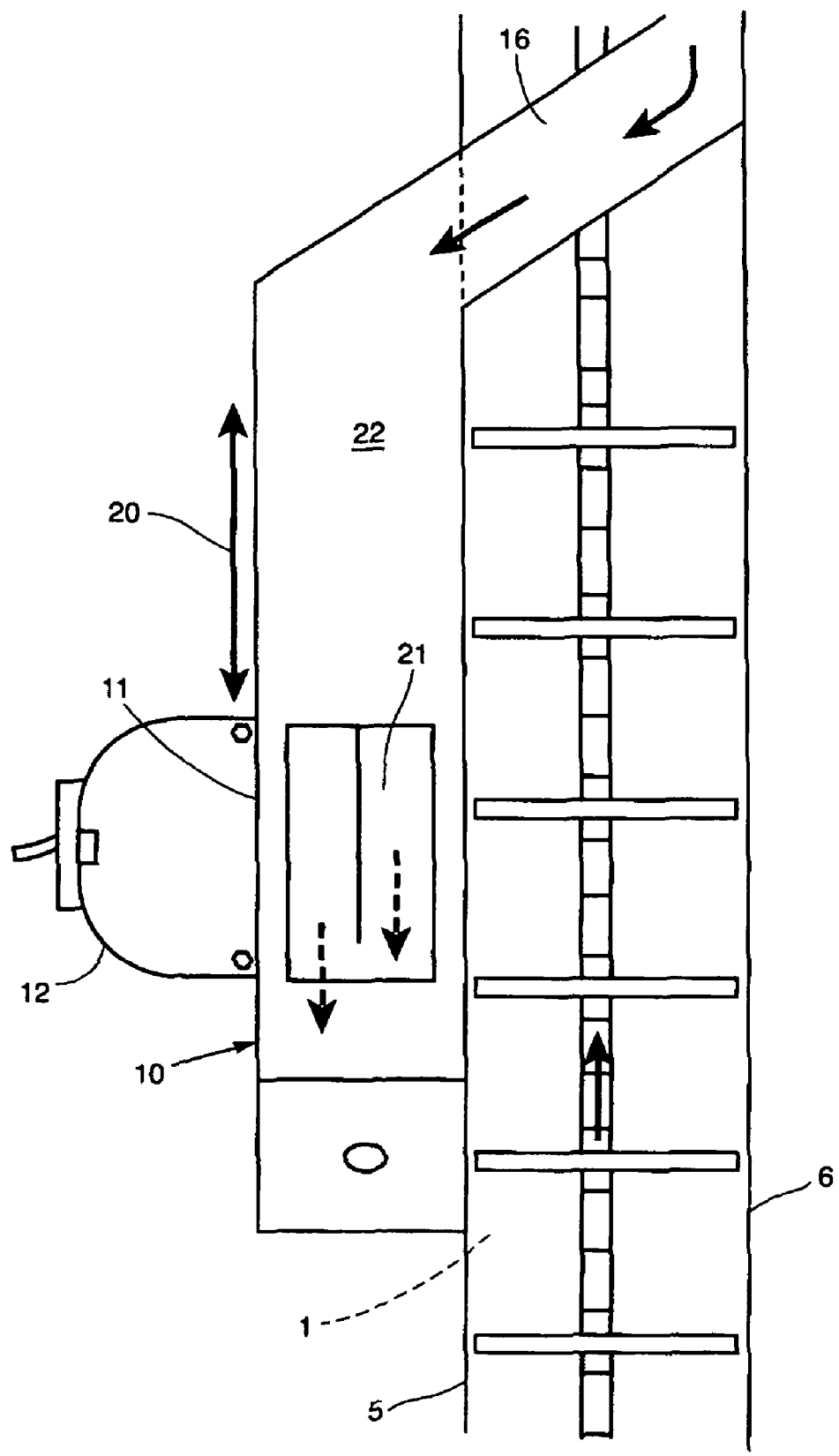
FIG. 2 is a view similar to FIG. 1 but rotated through 90°.

In the context of this description, the elevator is regarded as an essentially rectangularly shaped box, defined by two sets of perpendicular planes, wherein the side planes 5 and 6, shown in FIG. 2, of the elevator are the planes which are parallel to the plane of the drawing in FIG. 1 (i. e. the plane defined by the up and downward movement of the chain 4). The elevator is further defined by the outer plane 7 on the up-going side of the elevator and the outer plane 8 on the down-going side of the elevator. In the preferred embodiment shown in the drawings, the planes 5 to 8 correspond to the actual side walls of the elevator. With reference to FIGS. 1 and 2, plane 8 faces in the forward driving direction of the harvester whereas plane 5 faces towards the exterior of the harvester.

The analysis apparatus of FIGS. 1 and 2 comprises a housing 10 attached to one of the side planes of the elevator (plane 5 in the embodiment of FIG. 1). The housing 10 has a side window 11 to which a camera casing 12 can be attached, for taking images of crops accumulated in the area 21 in front of the window. The area 21 is the lower portion of the shaft-like analysis area 22 of the housing 10, into which the crops enter at the top. Preferably, the height of the shaft 22 is such that it comprises a portion 20 above the window 11, the volume of said portion 20 corresponding to at least the volume of the lower portion 21 where crops are accumulated in front of the window 11 when an image is taken. Typically, the height of the area 20 is at least equal to the height of the window 11 (e. g. when the shaft has a constant cross section, as shown in FIG. 1). The housing further comprises a return path comprising a return auger 13 for leading the crops back to the down-going path 2, through exit opening 14, after analysis. The auger is driven by a motor 17 or equivalent driving means. The movement of crops through the shaft 22 and the return path 13 is parallel to the side plane 5 of the elevator.

According to the invention, the crop entrance 15 into the analysing apparatus is not located in one of the side planes 5 or 6 (as is the case in the prior art), but in a plane parallel to the elevator's outer wall 7 on the up-going side, which in the current embodiment faces in the rearward driving direction of the harvester. The entrance can be present in the outer wall 7 itself, or in a plane essentially parallel thereto, and situated between the up and down-going paddles (see further). In the embodiment of FIGS. 1 and 2, the entrance 15 is present in the outer wall 7 of the elevator. The apparatus comprises a gutter portion 16 running partially along the outer plane 7, and partially further along the side plane 5 (as shown in FIG. 1) for bringing a supply of crops from the entrance 15 to the side plane 5 where the housing 10 is attached. The gutter portion 16 is sloped with respect to the elevator, for ensuring a supply of crops sliding down the gutter portion towards the top of the housing.

Figure 3:
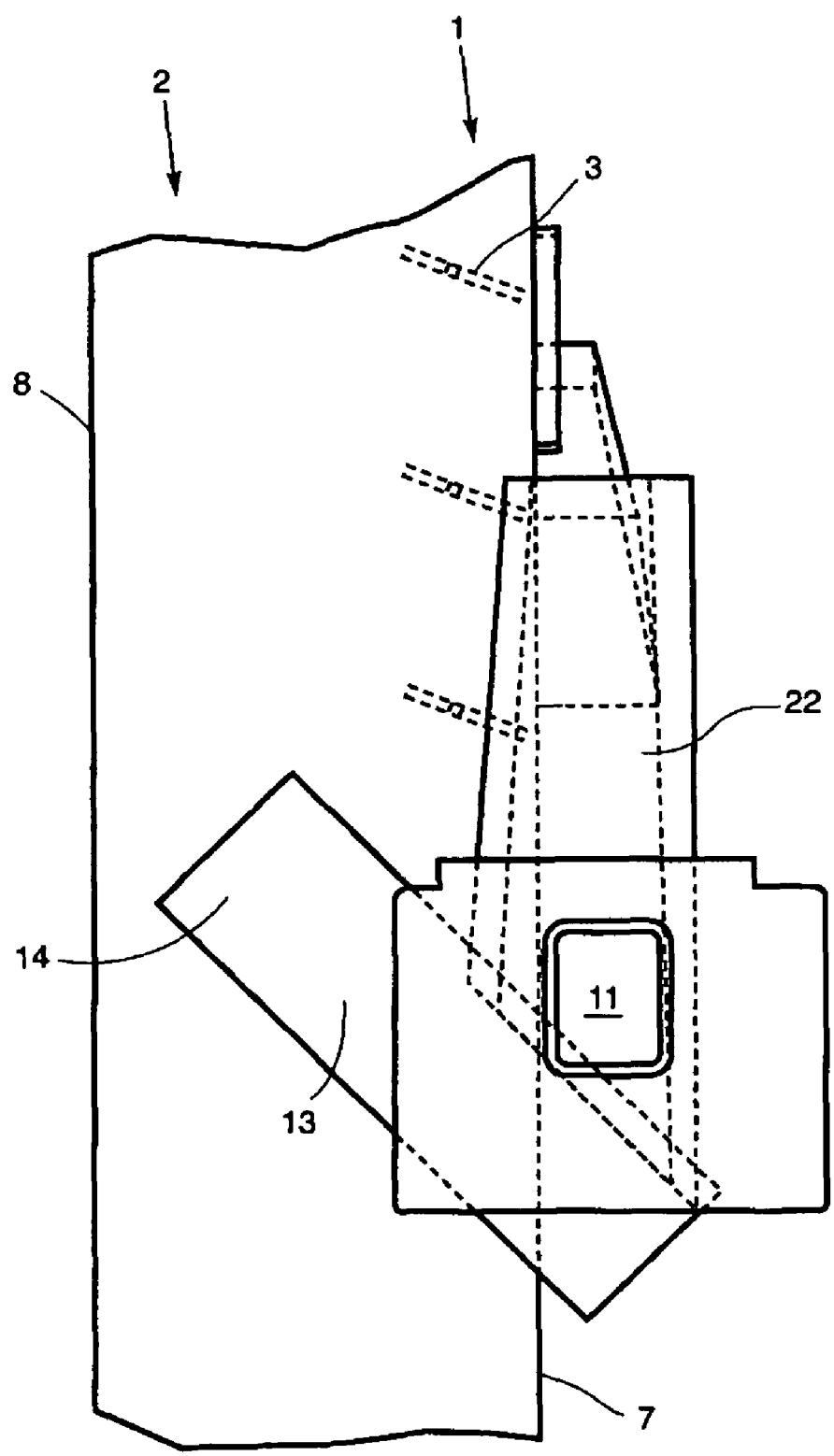
FIG. 3 is a view similar to FIG. 1, showing an alternative embodiment.
Figure 4:
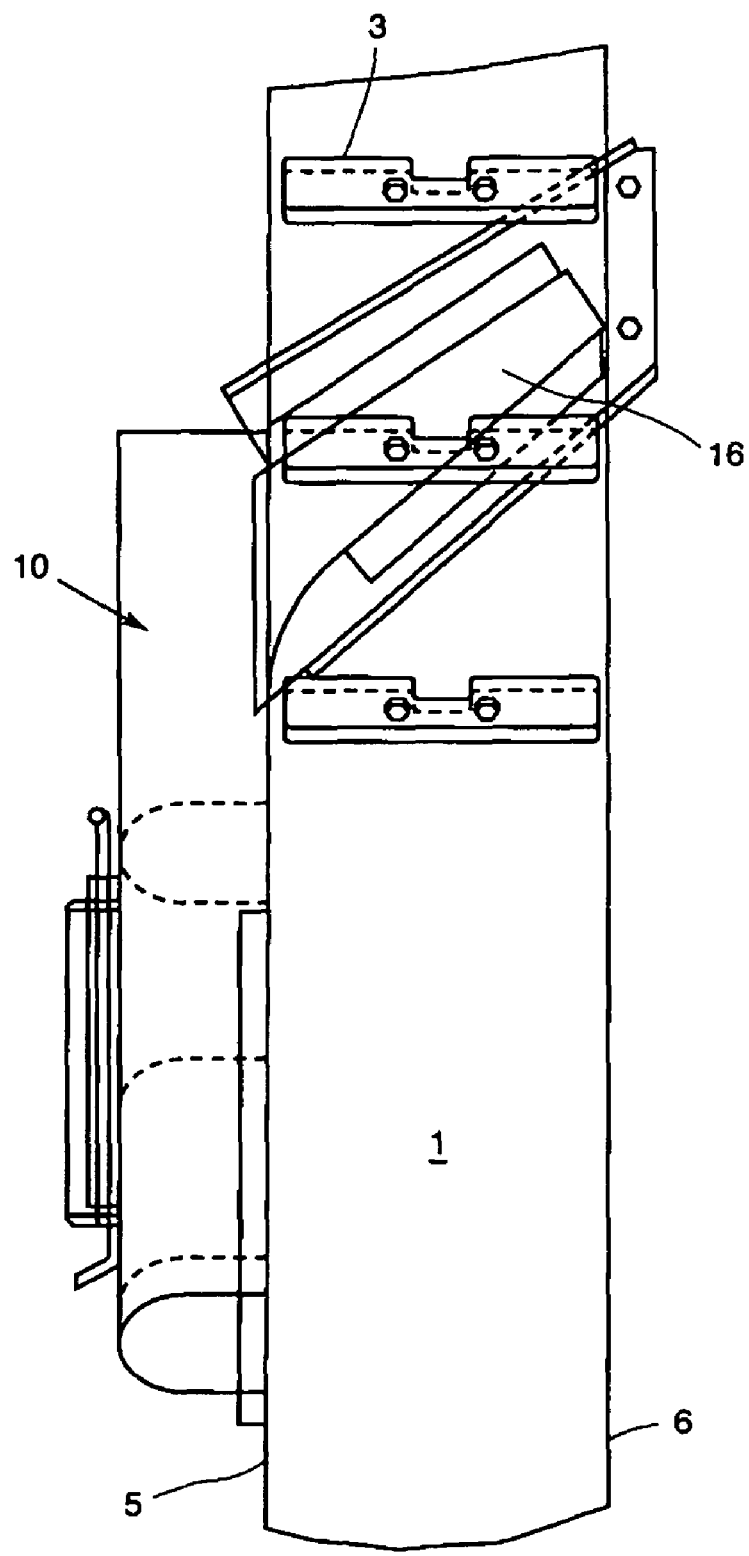
FIG. 4 is a view similar to FIG. 3 but rotated through 90°.
Figure 5:
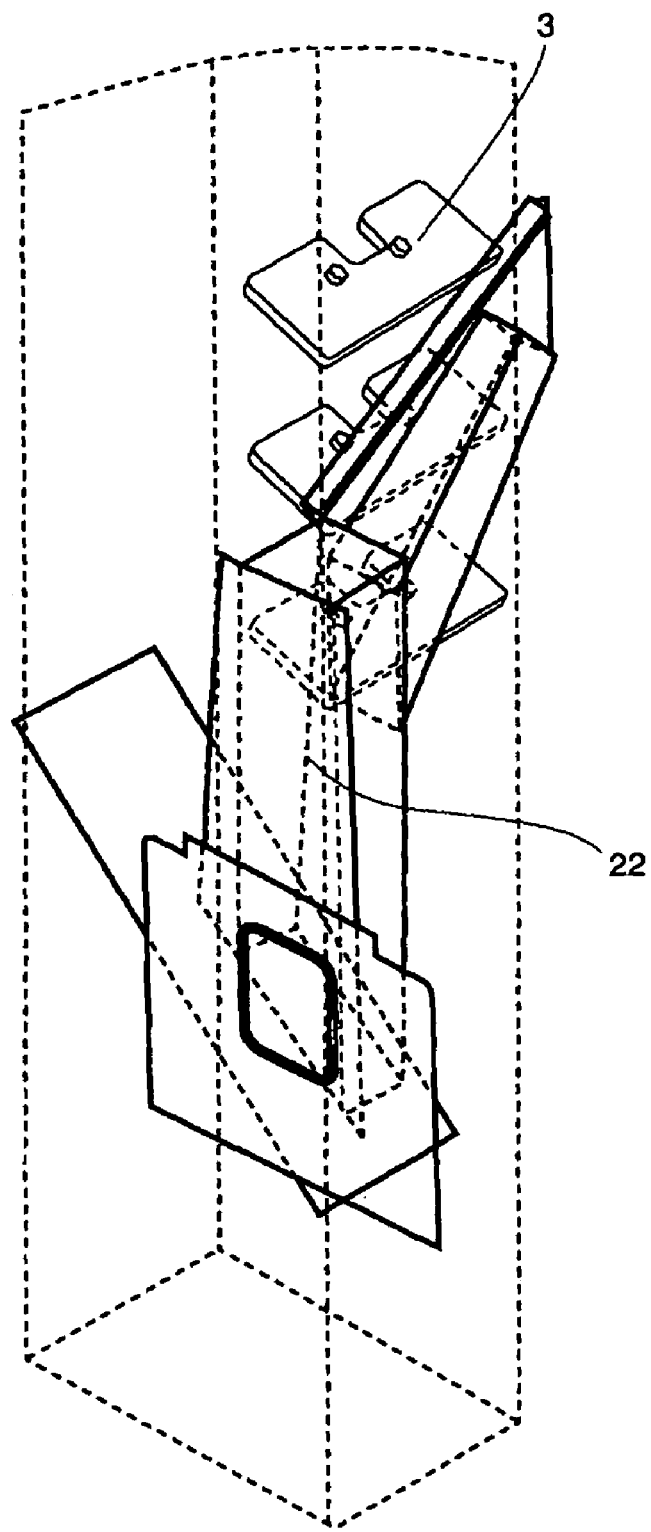
FIG. 5 is a perspective view of the embodiment of FIGS. 3 and 4.

FIGS. 3 to 5, in which like numerals refer to like parts, show an alternative location of the shaft 22. As best seen in FIG. 3, the shaft 22 is shifted to some degree towards the rear of the harvester whereby the window 11, as seen in the longitudinal direction of the harvester, is now located behind the rearward facing plane 7 of the elevator. As a result, a more simplified gutter 16, which only runs along plane 7, can be provided. In contrast, due to the more rearward location of the shaft 22, a somewhat longer return auger 13 needs to be provided.

As seen in FIG. 3, the paddles 3 are usually sloped downward with respect to the horizontal direction. This facilitates the crop movement into the entrance 15 and ensures a constant supply of crops into the analysing apparatus, even when the harvester is on a sloped surface. This in combination with the sloped gutter portion 16 and preferably with the presence of the upper portion 20 above the window 11, ensures that there is constantly an amount of grain in said area 20 above the window 11, during operation of the elevator. This ensures that images can be taken with a more constant frequency. Because the camera can detect on the image whether the bypass 22 is sufficiently filled, a level sensor is no longer required in the apparatus of the invention. As mentioned, in the embodiment of FIGS. 3 to 5, the sloped gutter 16 runs along the outer wall 7, and not along the side wall 5, because the shaft 22 is placed directly underneath the gutter portion. As seen further in FIGS. 3 and 5, the shaft 22 of the housing 10 is slightly diverging from top to bottom, which further reduces the risk of blockages and therefore ensures a more constant supply of crops to the area of the window 11.

Figure 6:
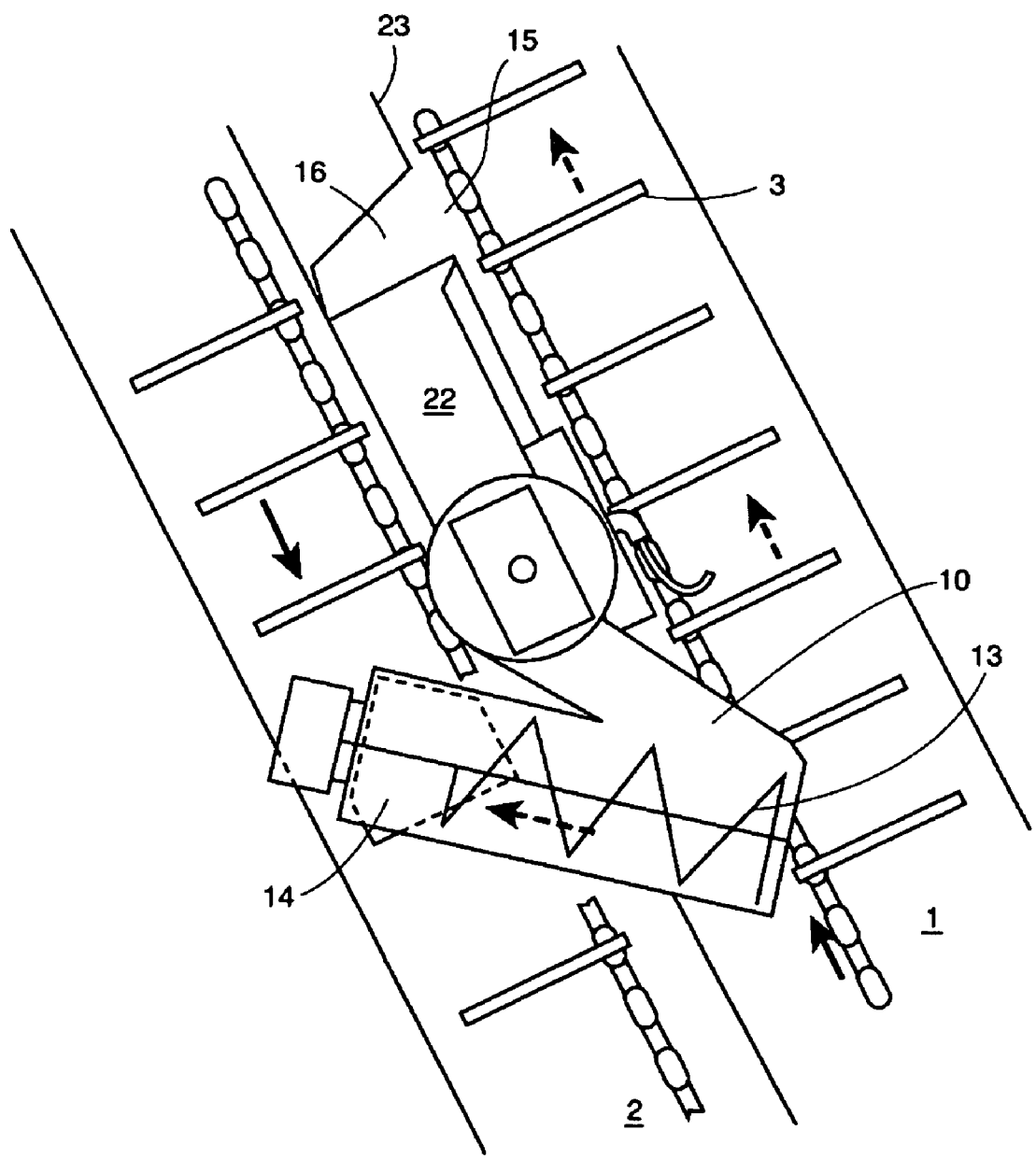
FIG. 6 is a view similar to FIG. 1, showing an embodiment wherein the crop entrance is located in between the up and down-going elevator paths.
Figure 7:
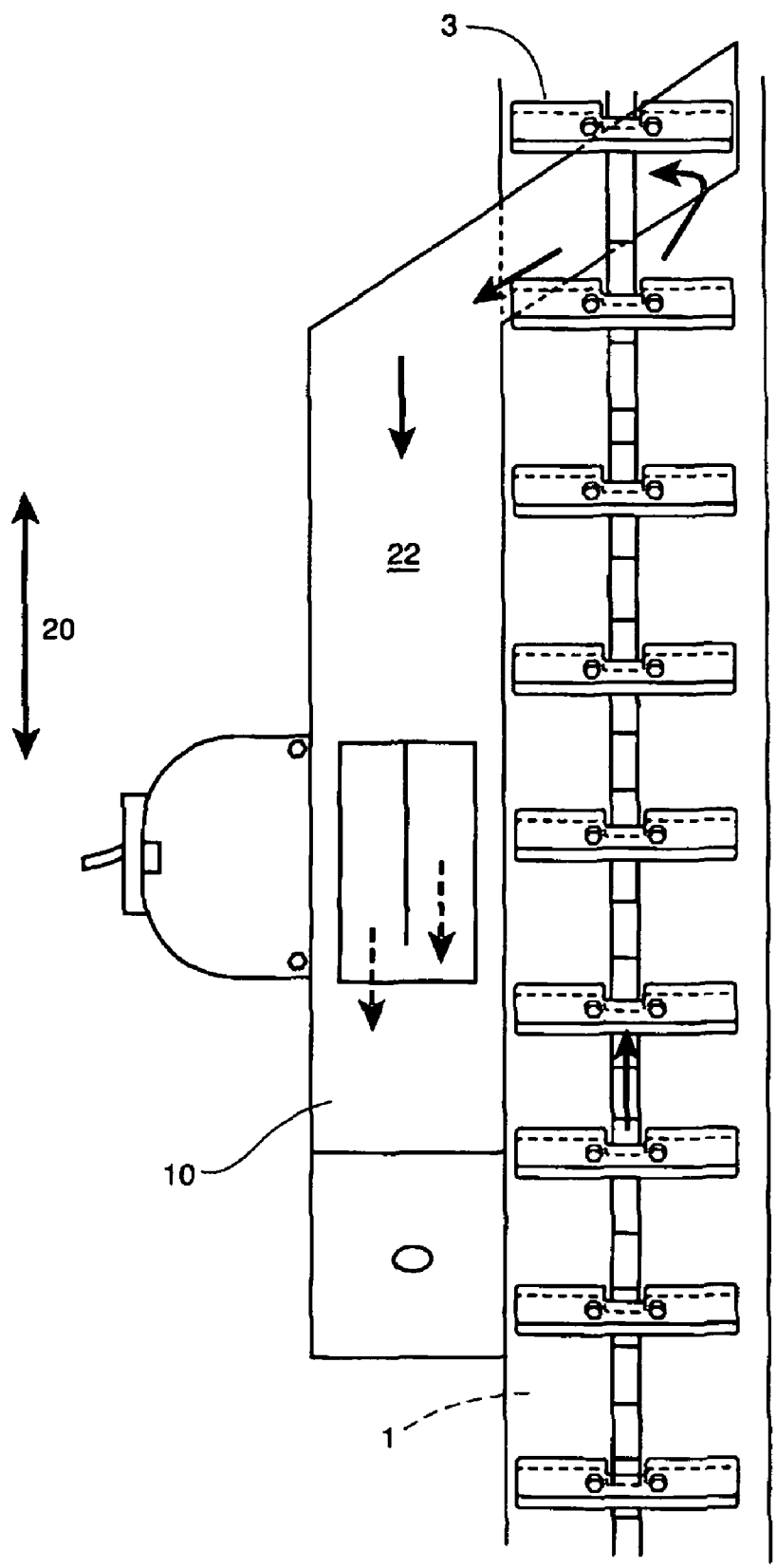
FIG. 7 is a view similar to FIG. 6 but rotated through 90°.

FIGS. 6 and 7 show a still further embodiment, wherein the crop entrance 15 is located in a separating wall 23, located between the up and down going paddles 3. This embodiment is preferred when the elevator is in a tilted position with respect to the harvester, as shown, and in which the paddles 3 are not sloped with respect to the elevator housing. This ensures a constant supply of crops towards the analyser, because of the tilted position of the elevator.

The invention claimed is:

1. An apparatus for analysing crop composition of crops moving in a grain elevator, said elevator comprising paddles and first, second, third and fourth walls forming a substantially rectangular-shape, the paddles being arranged to move up along the first wall at an up-going side of the elevator and down along the opposite third wall at a down-going side of the elevator, said apparatus comprising a crop entrance for entry of crops from the up-going paddles to the analysing apparatus and a housing including an analysis area for receiving and containing a volume of crops to be analysed, wherein the housing is coupled to the second wall, the second wall being substantially perpendicular to the first wall and a return path and return means for returning crops to the down-going paddles after analysis, and wherein the crop entrance is located in a plane essentially parallel to the first wall at the up-going side of the elevator, and gutter portion in communication with the crop entrance, wherein the gutter portion is sloped downwardly and wraps around the elevator extending from the first wall to the second wall for bringing crops from the crop entrance towards the housing, wherein the housing is positioned under the gutter portion.

2. The apparatus according to claim 1, wherein the analysis area of the housing comprises a lower portion for containing said volume of crops to be analysed, and an upper portion above said lower portion, the volume of the upper portion corresponding to at least the volume of the lower portion.

3. The apparatus according to claim 1, wherein the housing comprises a window for arranging a camera casing to said window, for taking an image of said volume of crops to be analysed.

4. The apparatus according to claim 1, wherein the analysis area is diverging from the top to the bottom of said area.

5. The apparatus according to claim 1, wherein the crop entrance is located in the elevator's first wall on the up-going side of the elevator.

6. The apparatus according to claim 1, wherein the gutter portion runs partially along said first wall on the up-going side and partially along the second wall essentially perpendicular thereto.

7. The apparatus according to claim 1, wherein the gutter portion runs along said first wall on the up-going side and wherein the analysis area of the housing is placed directly underneath said gutter portion.

8. The apparatus according to claim 1, wherein the paddles are inclined relative to the horizontal to improve the crop movement into the entrance and ensure a constant supply of crops into the analysing apparatus.

* * * * *